(12) United States Patent
Traverse et al.

(10) Patent No.: US 12,227,519 B2
(45) Date of Patent: Feb. 18, 2025

(54) PREPARATION OF MAYTANSINOL

(71) Applicant: CELGENE CORPORATION, Summit, NJ (US)

(72) Inventors: John Fitzgerald Traverse, Lebonon, NJ (US); Nareshkumar Jain, Flemington, NJ (US); Srinath Thirumalairajan, Bensalem, PA (US); Sanjeevani Ghone, Plainsboro, NJ (US)

(73) Assignee: CELGENE CORPORATION, Summit, NJ (US)

( * ) Notice: Subject to any disclaimer, the term of this patent is extended or adjusted under 35 U.S.C. 154(b) by 609 days.

(21) Appl. No.: 17/310,941

(22) PCT Filed: Feb. 28, 2020

(86) PCT No.: PCT/US2020/020452
§ 371 (c)(1),
(2) Date: Sep. 1, 2021

(87) PCT Pub. No.: WO2020/180709
PCT Pub. Date: Sep. 10, 2020

(65) Prior Publication Data
US 2022/0162230 A1 May 26, 2022

Related U.S. Application Data

(60) Provisional application No. 62/812,379, filed on Mar. 1, 2019.

(51) Int. Cl.
*C07D 498/18* (2006.01)
(52) U.S. Cl.
CPC .................. *C07D 498/18* (2013.01)

(58) Field of Classification Search
None
See application file for complete search history.

(56) References Cited

U.S. PATENT DOCUMENTS

| | | | |
|---|---|---|---|
| 4,308,269 A | 12/1981 | Miyashita et al. |
| 4,362,663 A | 12/1982 | Kida et al. |
| 6,333,410 B1 | 12/2001 | Chari et al. |
| 7,411,063 B2 | 8/2008 | Widdison et al. |

FOREIGN PATENT DOCUMENTS

| | | |
|---|---|---|
| WO | 2002/016368 A1 | 2/2002 |
| WO | 2016/061718 A1 | 4/2016 |

OTHER PUBLICATIONS

Asai M et al, "Isolation, chemical characterization and structure of ansamitocin, a new antitumor ansamycin antibiotic", Jan. 1, 1979, vol. 35, No. 9, p. 1079-1085.

Wayne C. Widdison et al, "Semisynthetic Maytansine Analogues for the Targeted Treatment of Cancer", Journal of Medicinal Chemistry, vol. 49, No. 14, Jul. 1, 2006, p. 4392-4408.

Kupchan S M et al, "Structural Reqirements for Antileukemic Activity among the Naturally Occurring and Semisynthetic Maytansinoids", Journal of Medicinal Chemistry, American Chemical Society, US, vol. 21, No. 1, Jan. 1, 1978. p. 31-37.

*Primary Examiner* — Samantha L Shterengarts
(74) *Attorney, Agent, or Firm* — Debora Plehn-Dujowich; Eckert Seamans Cherin & Mellott, LLC

(57) ABSTRACT

A scaled process of preparing maytansinol, FORMULA II, is provided by reacting a compound of Formula I, wherein R is selected from the group consisting essentially of alkyl, branched alkyl, aryl, alkenyl, alkynyl, as well as substituted variations thereof, with at least one organometallic reagent to produce the compound of Formula II; and, isolating the compound of Formula II.

11 Claims, 3 Drawing Sheets

FORMULA I

FORMULA II

AP-3; R= ≥75-80% ᶦPr,

~10% ᵗBu, 2-5% Et

Maytansinol, 1

PREPARATION OF MAYTANSINOL

CROSS-REFERENCE TO RELATED APPLICATIONS

This application is a National Phase of International Application No. PCT/US2020/020452, filed Feb. 28. 2020 which, is entitled to priority under 35 U.S.C. § 119(e) to U.S. Provisional Application No. 62/812,379, the disclosure of which are hereby incorporated by reference in their entirety as part of the present application.

FIELD OF THE INVENTION

A scaled process for the preparation of maytansinol from maytansinoids is provided which employs an organometallic reagent.

BACKGROUND OF THE INVENTION

Maytansine derivatives are highly toxic chemotherapeutic agents employed as payloads integral to Antibody Drug Conjugates (ADCs). 30% of ADCs in development employ maytansine derivatives. Chemical and Engineering News, 93:3,13 (2014). Maytansine derivatives are generally attached to a linker via an alcohol to yield a linker-payload entity which is then attached to an antibody. Maytansinol is a necessary intermediate for the formation of maytansine derivatives and hence the construction of maytansine-derivative-ADCs. Maytansinoids, Ansamitocins, e.g., Ansamitocin P-3 (AP-3), are natural source of a mixture of esters of maytansinol. AP-3, for example, is a polyketide antibiotic isolated from the microorganism *Actinosynnema pretiosum*. Each maytansinoid ester moiety can be removed to yield the alcohol, maytansinol.

The discovery of maytansine was originally reported by Kupchan, S M, J Am Chem Soc, 1354 (1972). Maytansinol was similarly reported several years later. Kupchan, S M, J Am Chem Soc, 5294 (1975); Kupchan, S M, J Med Chem, 31 (1978). Isolation of maytansinoids and the conversion of maytansinoids to maytansinol using lithium aluminum hydride is well known in the art. U.S. Pat. Nos. 4,308,269 and 4,362,663; Asai, M, Tetrahedron, 1079 (1979). Conversion of maytansinoids to maytansinol using lithium/sodium aluminum alkoxide hydrides and workup. See, e.g., U.S. Pat. Nos. 6,333,410 and 7,411,063; J Med Chem 4392 (2006).

Previous descriptions of removing various ester moieties to expose maytansinol employ aluminum hydride. Maytansinol 1 has previously been prepared by the reduction of AP-3 generally using 4-9 equivalents of lithium aluminum hydride (LAH; LiAlH$_4$), or a variant thereof such as lithium trimethoxyaluminum hydride (LiAlH(OMe)$_3$), which itself is prepared from LAH. J. Med. Chem. 49, 4392 (2006). Major drawbacks of this methodology however include (a) formation of overreduced by-product, and (b) formation of des-chloro-maytansinol. The current state of the art higher yielding procedures utilize LiAlH(OMe)$_3$ formed prior to the reaction by the addition of Methanol to LiAlH$_4$. The current high yield reaction generates multiple equivalents of hydrogen gas, which in turn requires specific safety equipment to minimize fire hazard. The current state of the art procedure requires the direct addition of methanol to LiAlH$_4$ to form LiAlH(OMe)$_3$. U.S. Pat. No. 6,333,410. The reagents cause difficulty in increasing scale of the exothermic reaction due to dangerous release of hydrogen. Current state of the art reactions also call for direct quench with a protic solvent, such as water or water/formic acid directly to the reaction mixture. This direct quench results in release of hydrogen gas which becomes more difficult to control as the reaction increases in scale.

SUMMARY OF THE INVENTION

The invention is directed to a scalable process of preparing maytansinol, FORMULA II,

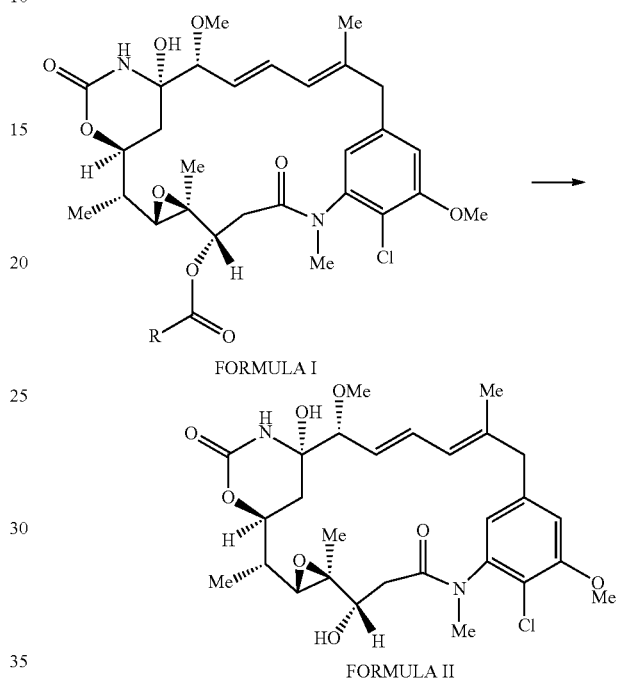

and related analogs, comprising reacting a compound of FORMULA I and related analogs, wherein R is selected from the group consisting essentially of alkyl, branched alkyl, aryl, alkenyl, alkynyl, as well as substituted variations thereof, with at least one organometallic reagent to produce the compound of Formula II, for example; and, isolating the compound of Formula II, for example.

In some embodiments, the compound of Formula I is provided from ansamitocins. In further embodiments, the compound of Formula I is provided as Ansamitocin P-3 (AP-3).

In some embodiments, the organometallic reagent is an organomagnesium reagent.

In some embodiments, the organometallic reagent is selected from the group consisting essentially of methyl magnesium halide, ethyl magnesium halide, propyl magnesium halide, butyl magnesium halide, and hexyl magnesium halide, where the halide is chloride, bromide, or iodide. In further embodiments, the organometallic reagent comprises magnesium bromide. In yet further embodiments, the organometallic reagent is methyl magnesium bromide.

In some embodiments, the organometallic reagent is a nucleophilic organometallic reagent. In further embodiments, the nucleophilic organometallic reagent is selected from the group consisting essentially of methyl-lithium, ethyl-lithium, n-butyl-lithium, hexyl-lithium and alkylaluminum reagents including but not limited to trimethylaluminum, and organocuprates.

Provided is a compound of Formula II prepared by reacting a compound of Formula I, wherein R is selected from the group consisting essentially of alkyl, branched alkyl, aryl, alkenyl, alkynyl, as well as carbon and heteroatom substituted variations thereof, with at least one organometallic reagent to produce the compound of Formula II; and, isolating the compound of Formula II.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Provided is a scaled process method for converting a mixture of esters of maytansinol, e.g., AP-3 to yield a substantial quantity of maytansinol for subsequent production of ADCs or other toxin-conjugated compounds. The conversion of Ansamitocins, e.g., AP-3, to maytansinol described herein employ an organometallic reagent. Prior methods for cleavage of Ansamitocin P-3 maytansinoids employ aluminum hydride reduction of the ester carbonyls. The method described herein, in contrast, employs the use of an organometallic reagent to attack the carbonyl of the esters resulting in the liberation of maytansinol upon aqueous workup. The new method is a key step in the conversion of naturally occurring Ansamitocin P-3 sources to an Antibody Drug Conjugate with a maytansine, for example, payload. See Examples I-III, infra.

Scaled process, as used herein, refers to commercial production scale of maytansinol. Production can range from about 100mg to 1 kg or more per batch of maytansinol.

Preparation of Maytansinol 1 from AP-3

An inert atmosphere, e.g, inert gas such as nitrogen or argon, substantially free of water and oxygen, is a preferred environment to conduct the reaction described herein. A wide range of temperatures apparent to those of ordinary skill can be used in the reaction steps. A range of about −80° C. to about 20° C. is contemplated. A range of about −40° C. to about −15° C. is preferred. Reaction time can be, for example, from about a minute or so to about four or more hours.

With reference to starting material, e.g., AP-3, (FORMULA I, for example) a wide variety of R groups on the starting esters are amenable to the reaction described herein.

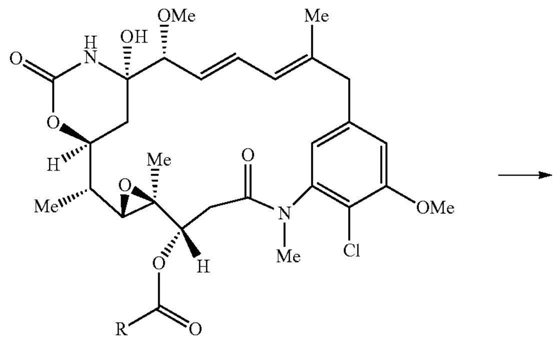

FORMULA I

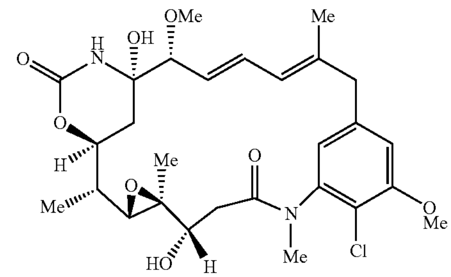

FORMULA II

R, for example, can be alkyl, branched alkyl, aryl, alkenyl, alkynyl, each containing from about 1 to about 20 carbon atoms, as well as variations and substituted variations thereof. The corresponding R groups in naturally occurring maytansinoids, e.g., AP-3 population, usually contain about 1-5 carbons.

The process described herein particularly employs an organometallic reagent, including but not limited to, methyl magnesium bromide. Organomagesium reagents, similar in function to methyl magnesium bromide, such as but not limited to ethyl-, propyl-, butyl-, or hexyl-magnesium bromide can be employed. Alternative alkyl magnesium halides may also be employed, where the halogens include chloride and iodide in addition to bromide. Also, nucleophilic organometallic reagents, including but not limited to methyl-, n-butyl-, or hexyl-lithium; alkylaluminum reagents, such as trimethylaluminum, and alkyl cuprates, can also be employed.

Tetrahydrofuran (THF) (oxolane) as well as other polar aprotic ethereal solvents including but not limited to 1,4 dioxane, diethyl ether, cyclopropylmethyl ether, cyclopentylmethyl ether, dimethoxyethane, methyl tent-butyl ether, diglyme, tetrahydropyran, or 2-methyltetrahydrofuran can also be employed as solvents in the process.

Various carbonyls including but not limited to acetone, methyl ethyl ketone or ethyl acetate can be employed to quench the excess organometallic reagent, e.g., methyl magnesium bromide. A proton source, for example, including but not limited to methanol, ethanol, propanol, butanol, or tent-butanol can also be employed.

The resulting precipitant can be dissolved by the addition of water, or a mixture of water with an organic solvent such as tetrahydrofuran, dioxane, acetone, or 2-methyltetrahydrofuran, for example. Alternatively the precipitant can be removed by filtration.

Water immiscible solvents known to those of ordinary skill can be used to extract the maytansinol including but not limited to ethyl acetate, isopropyl acetate, butyl acetate, methylene chloride, chloroform, 2-methyl tetrahydrofuran, or toluene.

An aqueous workup is performed. The resulting product-containing organic layer can be washed with water to reduce the inorganic content, particularly magnesium salts for example. The product containing organic layer can be washed with water followed by water saturated with sodium chloride, for example. The combined organic layer is then washed with water, followed by brine. Suitable alternative aqueous workups are known in the art. The residual water in the product containing organic layer can be reduced by sue of a dehydrating agent. $Na_2SO_4$, 3A or 4A molecular sieves, or magnesium sulfate, are preferred drying agents. Suitable alternative drying agents are also known in the art. Nevertheless, although preferred, employment of a drying agent is optional. Alternatively, for example, water can be removed by azeotropic distillation.

Isolation, Purification

Purification is preferred by normal phase column chromatography by eluting with a gradient of 1-10% v/v methanol in DCM. Other chromatography systems, e.g. reverse phase HPLC and SFC (Super Critical Fluid Chromatography) can be used. Different eluents known in the art for normal phase chromatography can also be used to purify the product, maytansinol. Crystallization can also be employed.

Figure 3:
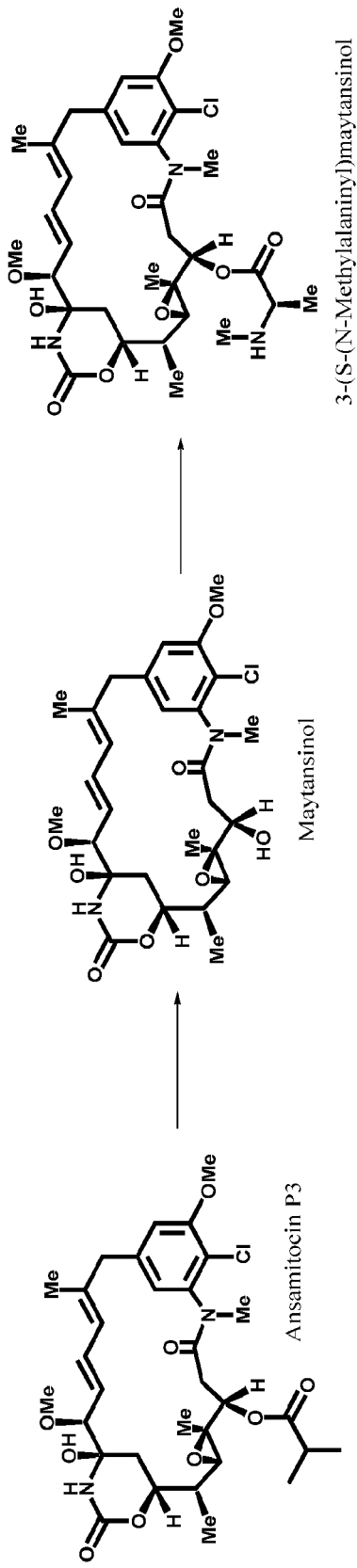
FIG. 3 shows Maytansinol, efficiently produced as described herein, can then be converted to 3-(S-(N-Methylalaninyl)maytansinol ester, or a derivative of 3-(S-(N-Methylalaninyl)maytansinol ester.

Maytansinol is often converted to 3-(S-(N-Methylalaninyl)maytansinol ester, or a derivative of 3-(S-(N-Methylalaninyl)maytansinol ester. An ester is reported to be important for activity. See FIG.3. Kupchan, S. M. et al., Journal of Medicinal Chemistry, Vol 21, No. 1, pg 31-37 (1978). This is then further conjugated to a linker for eventual conjugation with the monoclonal antibody (mAb) of the ADC.

EXAMPLES

AP-3 used in the following studies was determined (by LC-MS) to have a composition of ca. 75-80% isobutyl, ca. 10% tert-butyl, and ca. 5% ethyl esters.

Example I

Grignard reagents have been used extensively by synthetic organic chemists especially for modifying carboxyl functionality of esters, ketones, and aldehydes. An attempt was made in which AP-3 was treated with 3 eq. of methyl magnesium bromide (MeMgBr) at −30° C. and then warmed to 0° C. The reaction was monitored periodically by LC-MS and was observed to result in ca. 50% conversion to maytansinol 1 (+50% AP-3) after stirring for 3 h, but resulted in the formation of previously unknown impurities when stirred longer. Owing to this initial success, the reaction was repeated with 10-12 eq. of MeMgBr and found to result in ca. 90% conversion to maytansinol 1. Initially the reaction was quenched at 0° C. using aq. HCL solution. However, it was later determined that quenching the reaction with excess of either tert-butanol or acetone resulted in the formation of other impurities during quenching. When acetone was used for quenching, a precipitate was obtained, which was then dissolved by the addition of water followed by extraction of the product with ethyl acetate. Whereas when t-butanol was used, a homogeneous solution was obtained. Since the use of acetone as the quenching agent would result in tert-butanol as the by-product after addition of water, acetone was used in all subsequent reactions. The use of acetone also minimizes the release of methane gas upon quenching. Thus, the reaction was scaled-up using 250 mg of AP-3 and isolated ca. 160 mg (ca. 70% yield) of maytansinol 1 after purification by normal-phase column chromatography eluting with a gradient of 1-10% v/v methanol in methylene chloride (DCM).

Example II

The reaction using MeMgBr was attempted in DCM as the solvent, but was observed to be sluggish in that ca. 30% of AP-3 still remained even after stirring at room temperature (rt) overnight (16 h). An attempt was also made to improve the reaction using 13 eq. "Turbo Grignard" (mixture of iPr-MgCl+LiCl; 1.3 M solution in THF), but was observed to be sluggish and resulted in dehydrated maytansinol as the main product.

Example III

To a clean, dry 25 mL round bottomed flask equipped with a magnetic stirrer, was charged AP-3 (250 mg, 0.39 mmol) followed by THF (2.0 mL). The mixture was stirred under argon at rt for 15-20 min to give a clear homogeneous solution. The resultant solution was cooled to −30 ° C. and then MeMgBr (1.94 M; 2.4 mL; 4.72 mmol; 12 eq.) was added dropwise at −30° C. via syringe under argon. After the completion of addition, the reaction mixture was warmed to 0° C., at which point LC-MS analysis indicated mainly (≥90%) the desired product. At this point, acetone (10-15 mL) was added to the reaction mixture at 0° C. initially gradually and then in one portion later. A white precipitate formed, which was transferred to a breaker and then dissolved by the addition of water (15-20 mL). The resultant solution was extracted using ethyl acetate (5×25-30 mL). The combined organic layer was then washed with water, brine, dried ($Na_2SO_4$), and then concentrated to give a crude product, which was purified by normal phase column chromatography by eluting with a gradient of 1-10% v/v methanol in DCM. The fractions containing the desired product were pooled and concentrated to give 0.158 g (71%) of maytansinol 1 as a white solid.

Example IV

Typical conditions for an ester hydrolysis are aqueous bases. Aqueous bases fail to effect the result described herein, i.e:

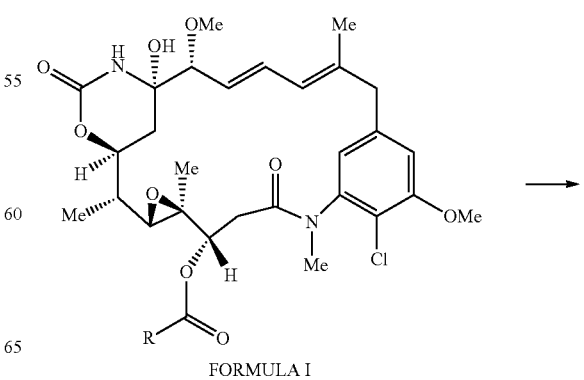

FORMULA I

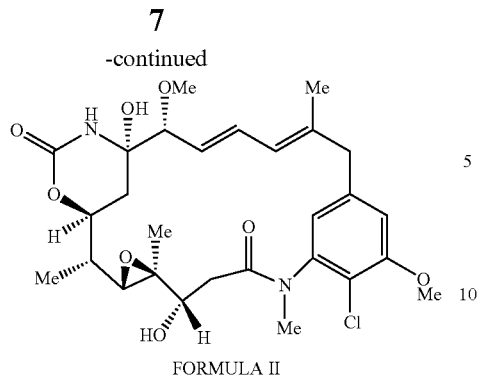

FORMULA II

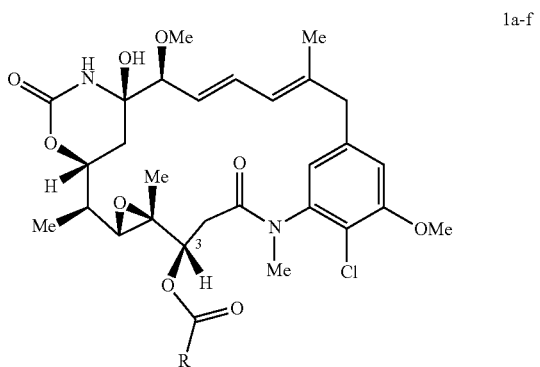

1a: R = N-acetyl-N-Me alanine: Maytansine
1b: R = acetate: Ansamitocin P-1
1c: R = proprionate: Ansamitocin P-2
1d: R = iso-butyl: Ansamitocin P-3
1e: R = sec-butyl: Ansamitocin P-3'
1f: R = iso-amyl: Ansamitocin P-4

Removal of the ester at C-3 yields secondary alcohol Maytansinol (2).

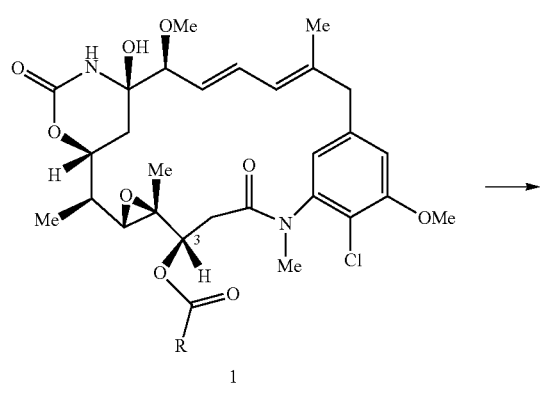

Figure 1:
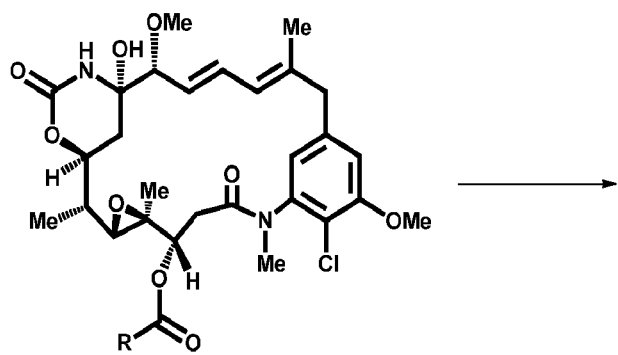
FIG. 1 illustrates the conversion of esters of maytansinol to maytansinol according to the process of the invention.
Figure 1:
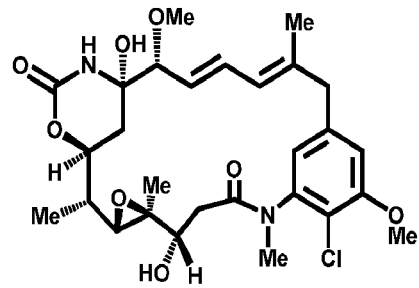
Figure 2:
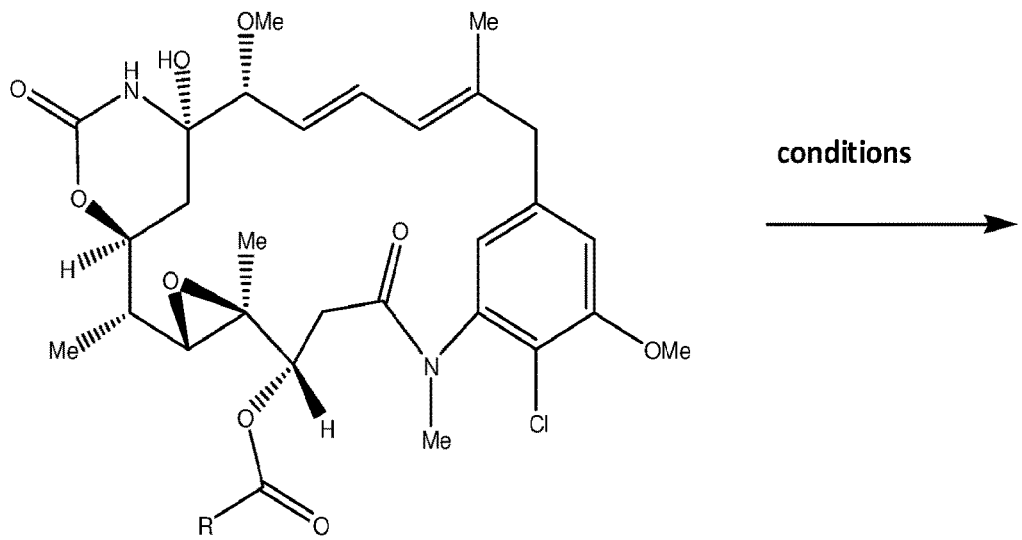
FIG. 2 illustrates the conversion of AP-3 to maytansinol in the presence of R-M wherein R=alkyl or branched alkyl; and, M=metal, e.g., Mg, Li, Al, Cu.
Figure 2:
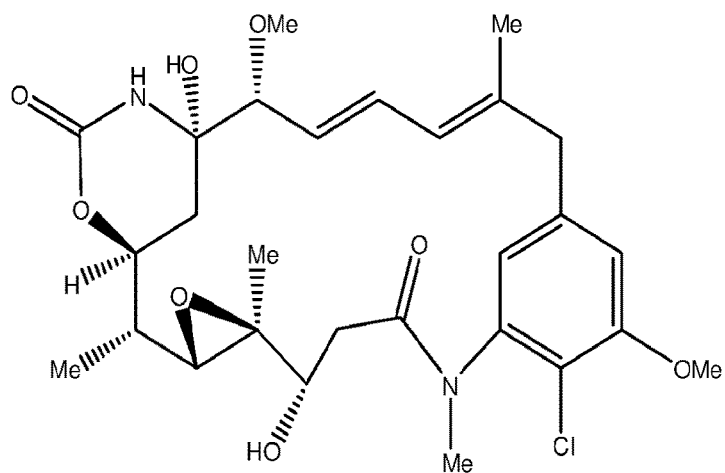

Aqueous bases do not work in this reaction. A summary of conditions previously attempted by experts throughout the years to effect the result described herein are set forth as follows:

Maytansine (1a) was first reported in 1972 by Kupchan et al. *J. Am. Chem Soc.*, 1354 (1972). An isolation of ansamitocins (maytaninoids) by Asai et al. from the broth of Nocardia assigned the nomenclature in FIG. 1 for the different esters at Carbon 3. *Tetrahedron*, 1079 (1979).

The revealed secondary alcohol is used to link maytansines to linkers used in Antibody Drug Conjugates. See Pillow, T. et al. *J. Med. Chem.* 7890 (2014). The first reported removal of the esters to form 2 was reported by Kupchan, et al. *J. Am. Chem Soc.*, 1354 (1972). LiAlH$_4$ in tetrahydrofuran was reported to convert Maytansine (1a) to Maytasinol (2) in 40% yield. Further details were provided by Kupchan et al. in 1978. *J Med Chem*, 31. The material from this procedure required three purifications, two preparative thin layer chromatographies, followed by an alumina column.

While multiple reported methods exist for the removal of an ester to an alcohol, it is well known in the art that the removal of the ester moiety from 1 to 2 is non-trivial. Greene, T. W., Wuts, P. G. M. Protecting Groups in Organic Synthesis, Third Edition, pg 149 to 178 (1999). Widdeson, et al., reported that common ester removal strategies degrade the compound. J. Med. Chem., 4392 (2006). For example, basic hydrolysis results in elimination of the ester to form a new olefin. Several alternative reductive reagents to LiAlH$_4$, such as DIBAL, NaBH$_4$, and Red-Al led to low yields and multiple side products. A wide panel of esterases was also unsuccessful.

Indeed, according to Widdeson, et al.

"Because the C3 ester group in maytansinoids is susceptible to elimination under mild basic conditions (pH>9) to give the α,β-unsaturated maytansinoid maysine, ester hydrolysis was achieved through a reductive cleavage process. The previously described method (Kupchan, S M, et al., J. Med. Chem. 21:31 (1978)) for the reductive cleavage of the C3 ester used lithium aluminum hydride and gave low yields of maytansinol with several side products. Several other reducing agents, including DIBAL, NaBH4, Red-A1, or Red-A1 +1 eq methanol, gave poor yields and multiple side products. Attempted enzymatic cleavage of the ester using a wide panel of commercially available esterases and lipases was also unsuccessful, with no detectable hydrolysis. However, the ester group in the ansamitocins was efficiently cleaved using the mild reducing agent lithium trimethoxyaluminum hydride, under controlled temperature (−30 to −40° C.), to give maytansinol in good yields. Higher reaction temperatures led to epoxide opening, whereas colder reaction temperatures resulted in a high proportion of unreacted starting material."

J. Med. Chem., 49:4392 (2006).

In 2001 Chari reported the use of lithium or sodium alkoxy hydrides as an alternative to LiAlH$_4$. U.S. Pat. No. 6,333,410. Chari and Widdison later reported that specific work up conditions are required to selectively break a bridged acetal intermediate to afford product 2 in high yields. WO 2007/05650. Alternative work ups lead to lower yields. All previously described procedures require silica gel chromatography to yield pure 2.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. A method of preparing a compound of Formula II

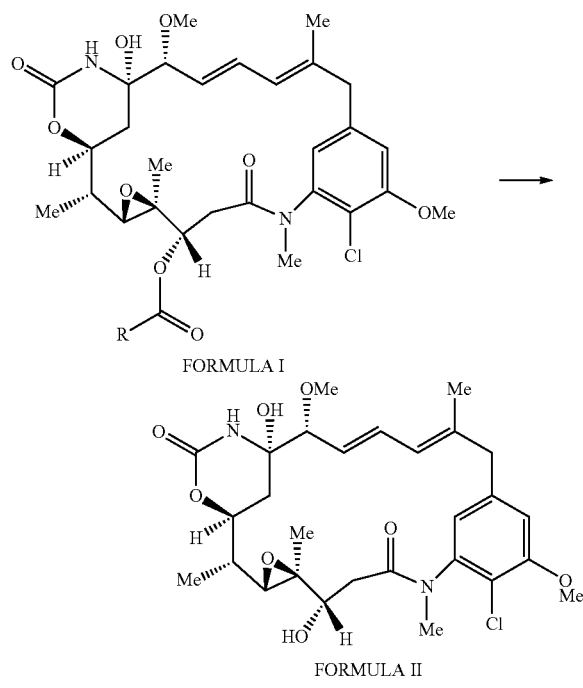

comprising reacting, in a polar aprotic ethereal solvent, a compound of Formula I, wherein R is selected from the group consisting of alkyl, branched alkyl, aryl, alkenyl, alkynyl, as well as substituted carbon or heteroatom containing alkyl, branched alkyl, aryl, alkenyl or alkynyl, with at least one organometallic reagent to produce the compound of Formula II; and, isolating the compound of Formula II.

2. The method according to claim 1 wherein the compound of Formula I is provided from ansamitocins.

3. The method according to claim 2 wherein the compound of Formula I is provided as Ansamitocin P-3 (AP-3).

4. The method according to claim 1 wherein the organometallic reagent is an organomagnesium reagent.

5. The method according to claim 4 wherein the organometallic reagent is selected from the group consisting of methyl magnesium halide, ethyl magnesium halide, propyl magnesium halide, butyl magnesium halide, and hexyl magnesium halide, where the halide is chloride, bromide, or iodide.

6. The method according to claim 5 wherein the organometallic reagent comprises magnesium bromide.

7. The method according to claim 6 wherein the organometallic reagent is methyl magnesium bromide.

8. The method according claim 1 wherein the organometallic reagent is a nucleophilic organometallic reagent.

9. The method according to claim 8 wherein the nucleophilic organometallic reagent is selected from the group-consisting of organocuprate, methyl-lithium, ethyl-lithium, n-butyl-lithium, hexyl-lithium and alkylaluminum reagents.

10. The method according to claim 1, wherein the polar aprotic ethereal solvent is selected from the group consisting of 1,4-dioxane, diethyl ether, cyclopropylmethyl ether, cyclopentylmethyl ether, dimethoxyethane, methyl tert-butyl ether, diglyme, tetrahydropyran and 2-methyltetrahydrofuran.

11. The method according to claim 9, wherein the nucleophilic organometallic reagent is trimethylaluminum.

* * * * *